United States Patent [19]

Hognestad

[11] Patent Number: 4,656,595
[45] Date of Patent: Apr. 7, 1987

[54] METHOD AND A DEVICE FOR MONITORING LARGE METAL STRUCTURES

[75] Inventor: Harek Hognestad, Haslum, Norway

[73] Assignee: Sentralinstitutt for Industriell Forskning, Blindern, Norway

[21] Appl. No.: 571,876

[22] PCT Filed: Apr. 18, 1983

[86] PCT No.: PCT/NO83/00011
§ 371 Date: Dec. 8, 1983
§ 102(e) Date: Dec. 8, 1983

[87] PCT Pub. No.: WO83/03675
PCT Pub. Date: Oct. 27, 1983

[30] Foreign Application Priority Data

Apr. 19, 1982 [NO] Norway ............................... 821257

[51] Int. Cl.⁴ ..................... G01N 29/04; G06F 15/36
[52] U.S. Cl. .................................... 364/507; 73/768; 73/775; 324/64
[58] Field of Search ................. 364/507, 512; 73/763, 73/768, 775; 324/64, 584, 65 P

[56] References Cited

U.S. PATENT DOCUMENTS

| | | | |
|---|---|---|---|
| 2,094,234 | 9/1937 | Drain | 324/64 |
| 2,326,352 | 8/1943 | Greenslade | 324/64 |
| 3,786,679 | 1/1974 | Crites | 73/775 X |
| 4,063,161 | 12/1977 | Pardis | 324/64 X |
| 4,101,827 | 7/1978 | Offner | 324/64 X |
| 4,353,255 | 10/1982 | Fukuda et al. | 364/507 |

FOREIGN PATENT DOCUMENTS 55-82060  6/1980  Japan.

OTHER PUBLICATIONS

Magnetic & Electrical Methods of Non destructive Testing; Lewis, D. M. pp. 126–129, Allen & Union Ltd. 1951, TA41024.

Primary Examiner—Felix D. Gruber
Assistant Examiner—H. R. Herndon
Attorney, Agent, or Firm—Wenderoth, Lind & Ponack

[57] ABSTRACT

A method and device for monitoring large structures so as to detect defects, e.g. cracks. An electric current is supplied to a steel structure which is equipped with contact points between which are measured voltage drops caused by the impressed current. A relatively large number of fixed contact points are used all over the area which is to be monitored. The voltage drops are measured between selected pairs of contact points and these voltage drops are compared with corresponding voltage drops that have been measured previously in the same manner when the structure was in an initial condition, preferably without any defects. The monitoring can this be performed by means of robust and simple devices which are relatively impervious to rough environments.

18 Claims, 9 Drawing Figures

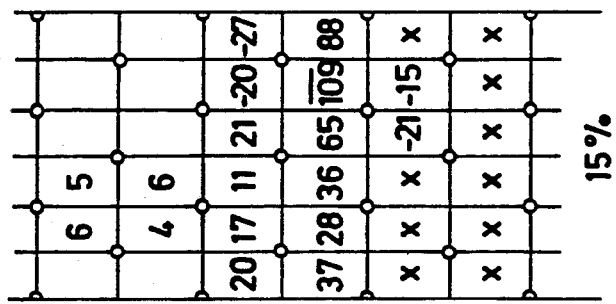
FIG. 5d. 15%
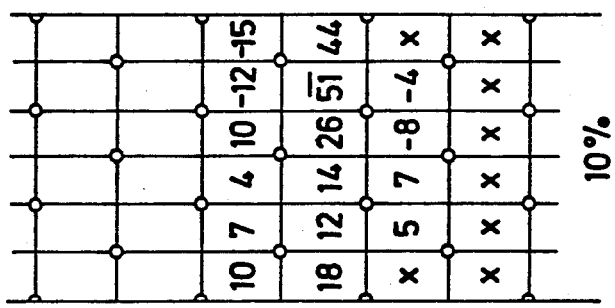
FIG. 5c. 10%
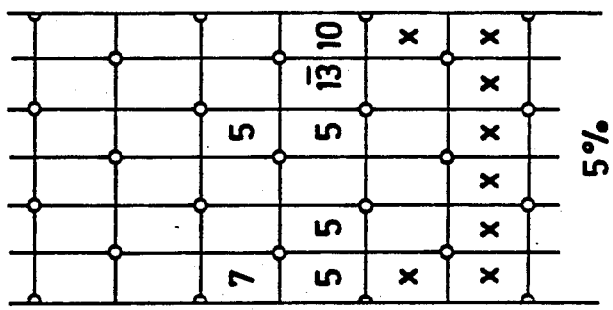
FIG. 5b. 5%
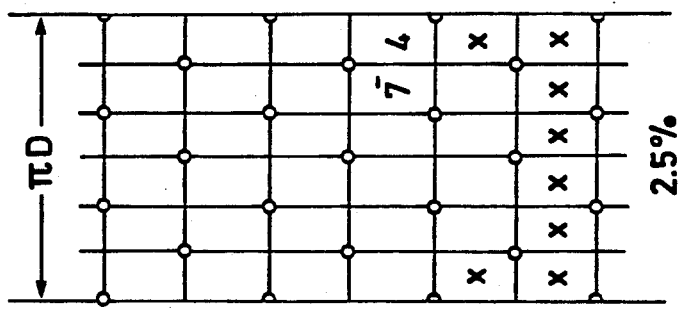
FIG. 5a. 2.5%

METHOD AND A DEVICE FOR MONITORING LARGE METAL STRUCTURES

BACKGROUND OF THE INVENTION

In recent years large metal structures, in particular steel structures, have been built with such large dimensions and have been used under so severe circumstances that the need for detection and localization of defects therein, e.g. cracks or fractures, has become urgent in many applications. Examples in this respect are large vessels and offshore petroleum production structures which occasionally have met with accidents that have increased the need for more accurate monitoring systems.

Various measuring principles of such monitoring systems have been suggested, i.e. methods based on vibration analysis, acoustic emission, ultrasonic systems, registration of magnetic fields as well as visual inspection. So far these methods have not been adequate in this connection, mainly because of the great strains to which the monitoring equipment can be exposed to, in particular under water. In addition to being resistant to such strains, it is also important that the monitoring systems do not entail prohibitive installation and maintenance costs, since the components or areas which are to be monitored often have very large dimensions. Systems that, for example, are based on the use of a number of transducers, e.g. for detection of vibration, acoustic emission or ultrasonic signals, may involve the mounting of a large number of transducers, each one representing a comparatively high expense and a risk of failure.

Another previously disclosed method for examination of cracks in structural parts or components is based on the measurement of the electric field that is produced in the structure. This so-called potential drop method is used for detailed examination of a crack that has been localized beforehand. The size or depth of the crack is determined by means of contact points on each side of the crack, between which the voltage is measured. The supplied current is either DC or AC with a low frequency. Different versions of the potential drop method have been published in German Patent Application No. 25 57 658 and in United Kingdom Patent Specification No. 804.323. In the former publication, a high frequency current supply is used, and the examination comprises measurements of the drop of potential as a function of the frequency. In the latter case, which in particular has been reported to concern surface cracks, a radio frequency potential is measured, which potential occurs between two separate electrodes that are moved on the surface of the structure while an oscillating electric current is supplied thereto from a source of radio frequency. Such an arrangement with movable electrodes which are to be guided all over the monitoring area cannot, however, be used for the purpose mentioned above.

SUMMARY OF THE INVENTION

The object of the present invention is to monitor, under difficult and perhaps extreme conditions, e.g.—on offshore oil drilling rigs and petroleum production platforms, large areas or surfaces of steel structures in the course of long periods of time and to detect possible defects, such as cracks or corrosion damage, as they may develop. Basically the invention involves application of the potential drop method, as the structure or a section thereof is supplied with an electric current and voltage drops are measured between contact points on the surface of the structure when the structure is in an initial condition and preferably does not have any defects. Similar measurements of voltage drops are performed on the structure when in use, which measurements are compared with the measurements from the initial condition.

The new feature of the present invention resides in the fact that the structure or a section thereof is equipped with a comparatively large number of fixed contact points arranged in a pattern with a relatively uniform distribution all over the structure or over the section which is to be monitored, and in the fact that measurements are performed on supplying an electric current through at least two contact points or electrodes on the structure so as to measure the voltage drop between pairs of contact points selected from an essential portion or all of said contact points, the total picture of deviations between measurements from the initial condition and those from said performed measurements being included in the detection and localization of any defects.

In such a method, a characteristic signature of the structure is thus determined when the structure is in an initial condition and does not have any defects. During the operation of the structure similar measurements are performed and are compared with said signature. Possible deviations are calculated, e.g. in parts per thousand of the voltage drop, and presented in an appropriate manner.

An advantage of this method is that delicate sensors or transducers are not required. The contact points arranged on the structure may be shaped as strong steel bolts, fixed to the structure by welding. When appropriately designed and protected against corrosion, such contact points will function without any faults throughout the entire estimated lifetime of the structure.

Another advantage in many applications stems from the fact that steel and other metals, compared to salt water, constitute extremely low ohmic systems which are insensitive to leakage currents in the water. Obviously, this is important when it comes to offshore structures such as oil drilling rigs, petroleum production platforms and ship hulls.

It is possible to detect small cracks before they have got such sizes that there is a danger of break down of the structure. Transverse cracks for instance, can be detected even though less than 5 percent of the cross section of the material in a larger steel tube has been lost. Longitudinal cracks in such a tube may be detected by means of a number of sources for supplying the excitation current to the structure, or rather by connecting the same source to different pairs of current supply electrodes. It is also possible to design and arrange the contact points so that a greater number of these points or all of them by turns and in pairs can be used to feed the excitation current to the structure.

In principle, it is possible to use a DC as well as an AC source in this method. Application of a stationary DC source results in certain disadvantages, primarily because thermoelectric potentials may cause disturbances, and because of high stability requirements in the necessary electronic circuits. The voltage drops which occur between two contact points are usually measured in microvolts, in the order of magnitude, which means that amplification will always be necessary. Furthermore, it is desirable to measure the voltage drop at a great accuracy, e.g. at an accuracy of about 1 part per thousand. These circumstances are the reason why an AC signal with an appropriate shaped curve and frequency is preferred, although some additional and undesirable effects are then incorporated and complicate the measuring principle to some degree. Nevertheless, such an embodiment may involve an advantage as far as the measurement technique is concerned. Consequently, an excitation current shaped as a rectangular wave has been chosen.

The excitation current gives rise to a voltage drop because of the resistivity of the structural material. This voltage drop will be shaped in the same way as the excitation current and is primarily the basis of the measurements in the course of monitoring. As indicated above, some additional effects will occur, which effects may be considered to represent disturbances, dependent on the circumstances. Such effects are caused by electric induction in the measuring cables as a result of alterations of the excitation current and of skin effect in the structural part when the current alternates rapidly and gives rise to high frequency components. The appearance of the skin effect causes high or low current density in the surface (dependent on whether we consider the outer surface or the inner one of a tube, for example). This increased current density in turn results in a transient signal that dies more or less slowly, dependent on the geometry of the structure and on its electric and magnetic properties.

The considerations above form a background of a choice preferably to use such a low frequency, or pulse frequency respectively, that transients which are initiated by the rising or falling current, die before the current again alternates.

If the excitation current is kept constant for a certain period of time, a stationary condition will eventually occur. In that case, the measuring signal will be given only by the current distribution in the structure and the resistivity of the structural material, i.e.—the case corresponds to the application of a pure DC excitation. On measuring the difference in the signals between each half period of the alternating current in such a stationary condition, the unfortunate influence of signals which are not associated with the excitation current such as thermoelectric potentials, drift in an amplifier, etc. is eliminated as well.

Furthermore, it is expedient to perform relative measurements, e.g. by performing additional measurements at even intervals of the voltage drop across a pair of reference electrodes which should be positioned in an area on the structure where cracks will likely not occur. Thus, it is in principle possible to obtain an effective compensation for any changes in the excitation current as well. Such relative measurements may compensate for lots of undesirable effects, particularly if the same amplifier is alternately coupled to the measuring points concerned. Further features of the method reported above and of the device for performing this method will be apparent from the following description with references to the attached drawings, and from the claims.

BRIEF DESCRIPTION OF THE DRAWINGS

FIGS. 5a–5d are possible ways in which the monitoring results can be presented.

DESCRIPTION OF THE PREFERRED EMBODIMENT

Figure 1A:
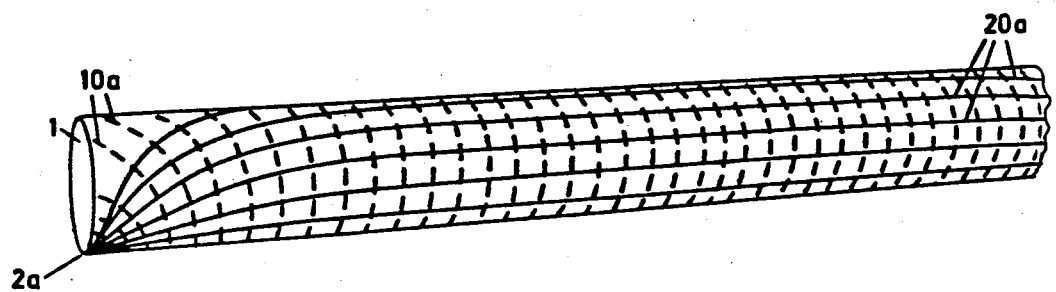
FIGS. 1a and 1b respectively show an example of a tubular structural part with a drawn image of an electric field that corresponds to a situation (FIG. 1a) void of defects and (FIG. 1b), with a field image affected by a defect (transverse crack).

In FIG. 1a, a length of a tubular structural part has been shown, the right end of which having been cut off. A current supply point 2a is shown at the left of the tubular part, while a corresponding contact point is provided at its right end; not shown. It is presupposed that the tube has no defects, e.g. cracks that may influence the distribution of the electric current and field and thereby the drop of potential along the tube. Equipotential lines are indicated by dotted lines 10a in FIG. 1a, which lines show the course of the electric field in the tube, while the continuous lines 20a illustrate the current paths in this rather idealized case.

Figure 1B:
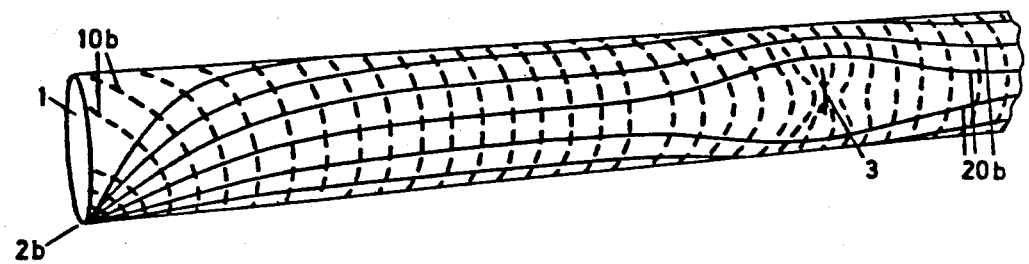

In FIG. 1b, the same tubular part has been shown in a situation where a crack 3 has developed transverse to the length direction of the tube. On supplying an electric excitation current in the same way as in FIG. 1a, a changed image of the field will be produced due to the crack 3, as it appears from the modified course of the equipotential lines 10b and current paths 20b respectively, around the crack 3. These changes are largest close to the irregularity represented by the crack 3, which irregularity is the reason why the current paths are displaced. However, the effect can be measured a certain distance from the crack too, dependent on the ability of the measuring equipment to detect small alterations of voltage.

In FIGS. 1a and 1b, which are disclosed only as a mere elementary and simplified explanation of the principle forming the basis of the invention, the image of the electric field in FIG. 1a can be considered the original signature or initial condition which the structural part possesses when the monitoring is started. Thus, the structural part is preferably void of defects in this initial condition. When e.g. a crack 3 as shown in FIG. 1b developes in the course of some time of monitoring, a changed image of the field appears, which image can be detected. The voltage drops or differences having been measured in this situation can be compared with the signature according to FIG. 1a for determination and localization of defects represented by deviations between the two series of measurements.

Figure 2:
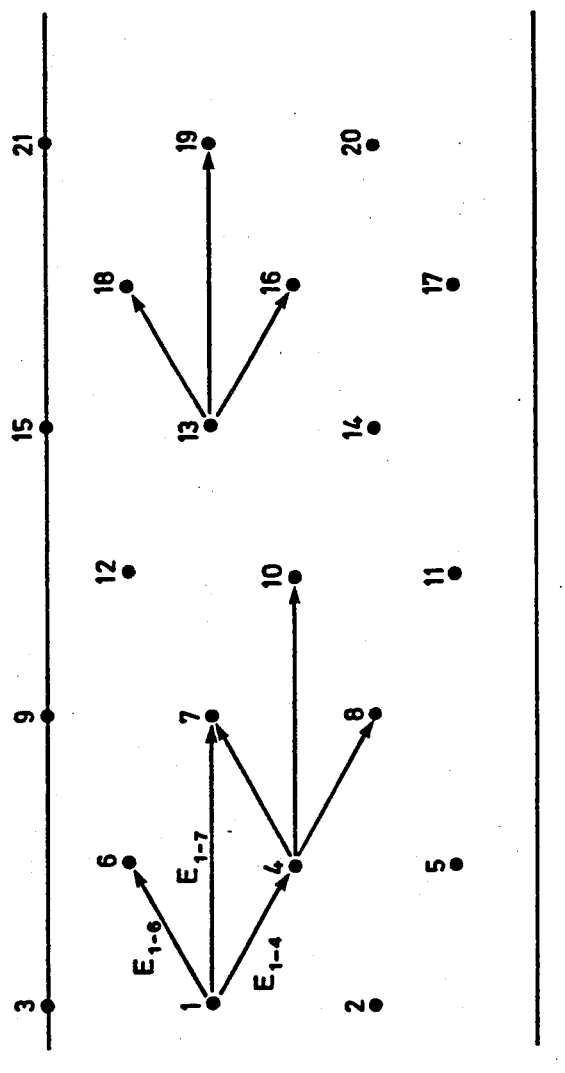
FIG. 2 is an arrangement or pattern of contact points for detection or monitoring of a tubular part as shown in FIGS. 1a–1b, the wall of the tube being unfolded.

FIG. 2 shows examples of locating a number of measuring or contact points denoted 1–21 on a tube as shown in FIGS. 1a–1b, but unfolded in FIG. 2. As it appears from this figure, the contact points are arranged in a regular pattern with sets of three points distributed along the circumference of the tube and in mutually spaced relationship to neighboring points in different directions. The measurements of voltage drops in such an arrangement can be performed in groups from selected measuring electrodes as outgoing points, e.g. from the points 1, 4 and 13 as indicated by arrows. The measurements in group 1 are done e.g. in relation to the arrows $E_{1-6}$, $E_{1-7}$ and $E_{1-4}$, respectively. The excitation current is supplied in a way that corresponds to the manner shown in FIGS. 1a and 1b, i.e. in the longitudinal direction of the tubular part.

Figure 3:
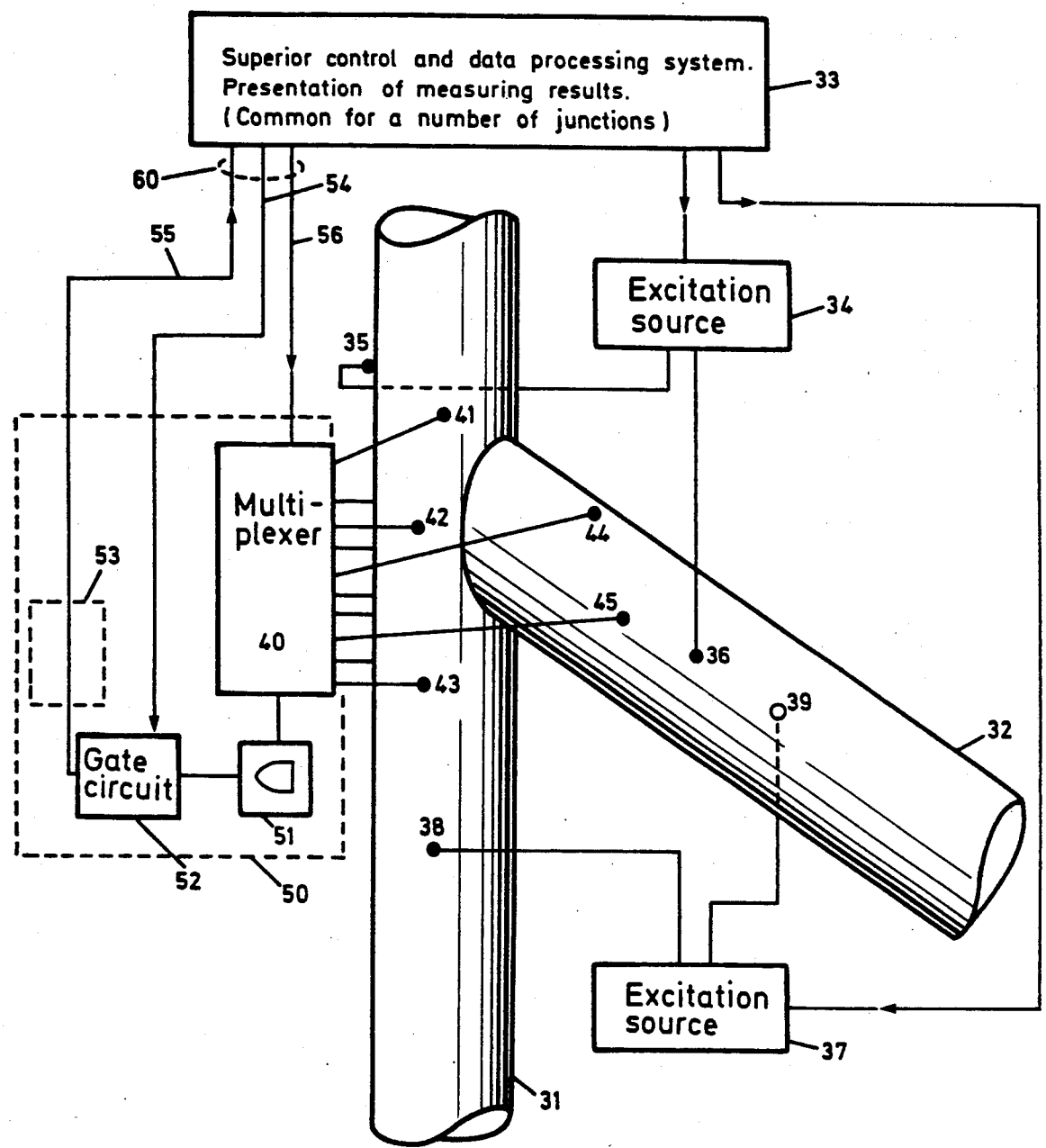
FIG. 3 is an embodiment for monitoring a junction in a structure consisting of tubular members.

FIG. 3 shows diagrammatically how the measuring method can be applied in practice to monitor a tubular junction in which an inclined tube 32 has been welded to a vertical tubular shaft 31. Such a junction, e.g. on a drilling rig, represents a type of a structural section for which monitoring is of great importance in order to detect early any defects that might develop in course of operation of the rig.

The monitoring is controlled by a superior control and data processing system 33 which possibly can be a common system for a number of such sections or areas on the drilling rig. Additionally, the control system 33 comprises means for presentation of the measuring results; not shown in the figure.

Two excitation sources 34 and 37 with associated contact points or feeding electrodes 35 and 36, and feeding electrodes 38 and 39 respectively, have been shown to illustrate how the excitation current is supplied to the junction. With such an arrangement two alternative possibilities of supplying current are available, each one having its own original structure, i.e. the image of an electric field in the initial condition.

The multiplexer 40 is controlled by the control system 33 through a conductor 56, and delivers consecutive signals from the different contact points 41-45 etc. to an amplifier 51. The output of amplifier 51 is connected to a gate circuit 52 which in a similar manner is controlled by the control system 33 through a conductor 54, serving to allow the desired portions of the signals to pass. This is to be explained further by reference to FIGS. 4a -4c. In addition to the gate circuit, a box 53 is indicated; the box 53 may be an A/D converter or alternatively may be a microprocessor that performs a certain processing of the measuring signals in the electronic unit 50 before the signals are delivered through a conductor 55 to the superior control and data processing system 33 for possible further processing and registration or presentation of the measuring results.

The connections between the control system 33 and the electronic circuit 50 can, as the case may be, comprise more than the three conductors 54, 55 and 56 shown in FIG. 3, dependent on which functions the unit 50 shall serve. The figure indicates that these connecting cables may have the form of a databus 60.

In case the circuit 53 is a microprocessor, this processor can do the operation of the multiplexer 40 so as to change-over to the proper measuring points simultaneously as the processor provides for the first processing of the measured signals. When the electronic unit 50 is located fairly close to the section to be monitored, the path of conductors to the contact points becomes simple and practical. The same is achieved when the excitation sources are located in proximity to the same section. A particular possibility consists in using the same contact points both for measurement of voltage drops and for supply of excitation current. In that case the electronic unit 50 comprises the excitation source as well, and the multiplexer 40 has to be constructed in such a way as to be capable of transmitting the higher currents of the excitation source. Such an arrangement enables the system to give much more freedom of establishing a series of different signatures for each area to be monitored so that separate paths of excitation currents can be arranged to detect special types of defects, e.g. longitudinal cracks.

The necessary excitation current depends on the thickness of the structural material to be monitored; for a tube with a wall thickness of 25 mm, the excitation current should be for instance 30 amperes, or higher. This rule goes for rectangular wave shaped alternating currents with relative low frequencies, e.g. 1-2 Hz.

The superior control and data processing system 33 may mainly consist of a mini computer, e.g. a relatively powerful desk top computer. The most important tasks for this computer may be:

Communication with local excitation sources, electronic units and possibly microprocessors, as well as selection according to a certain program of each section from among a number of sections to be monitored.

Storage of signatures.

Calculation of deviations from the respective signatures.

Presentation of deviations.

Calculation of average values and presentation of these values.

Trend-analysis of minor irregularities in the measured values.

Possible graphical presentation of data, preferably printed in colors.

Figure 4:
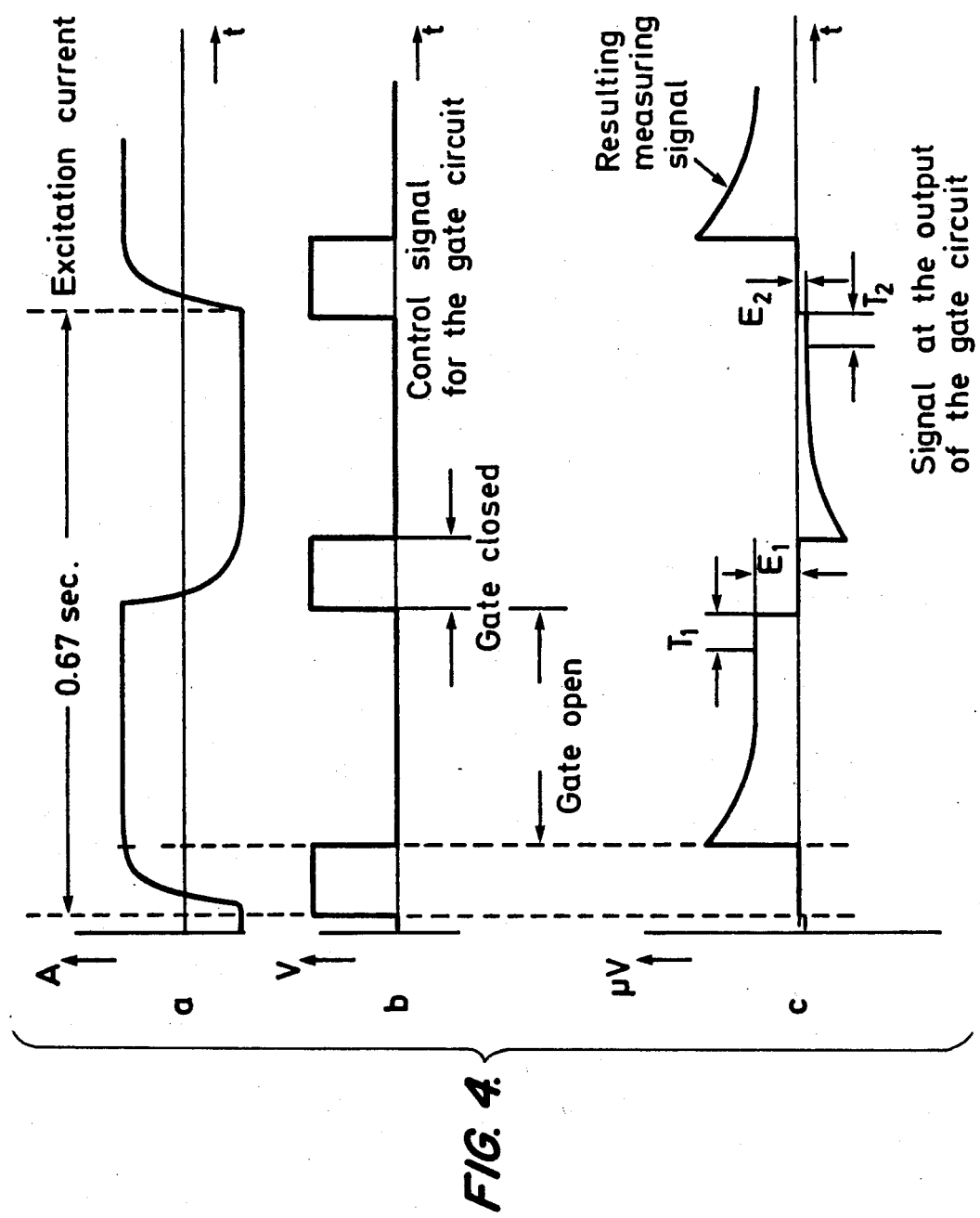
FIGS. 4a–4c illustrate shapes of curves on excitation currents and other signals which occur in a practical performance of the present invention.

FIG. 4a shows a rectangular wave shaped excitation current (AC) with frequency of 1.5 Hz, i.e. a period of 0.67 sec. FIG. 4b shows how the operating signal on a gate circuit, such as the gate 52 in FIG. 3, may be in order to block out undesired portions of the resulting measuring signal, since this signal will involve transients that may dominate the operation of the electronic circuits.

The resulting measuring signals at the output of the gate circuit is shown in FIG. 4a. The voltages that are to be measured are denoted $E_1$ and $E_2$, and time intervals $T_1$ and $T_2$ respectively, are shown for each half period. It appears from FIG. 4c that the measuring signal in the time interval $T_1$ has reached a constant value after the transient portion of the signal at the beginning of each half period had died. The same goes for the time interval $T_2$. As mentioned above these transients are caused by different effects, such as induction in the measuring cables, skin effect, etc. The value which is to be determined is $E=E_1-E_2$. It is desirable to determine this value as accurate as possible, preferably at an accuracy of approximately 1 part per thousand or better. At least the relative accuracy between a measurement concerning one group of contact points (see the description of FIG. 2) and a measurement across a reference pair of electrodes ought to be in this order of magnitude.

Different kinds of noise may result in inaccuracies of the measurements. The main sources of noise are:

Signals being induced in the measuring loop due to the electric installations (cables to the contact points and the associated structural part). Mainly, such a noise occurs in two different ways, namely:
  (a) More or less continuously at the line frequency and its harmonics. The dominating components are often 50 and 150 Hz.
  (b) Transients occurring when switching electrical apparatus on and off.

Noise in the amplifier.

Drift in the amplifier, multiplexer, etc. The required stability in such circuits and units is related to the period of time which is needed to perform a complete measurement, i.e. that the measurement includes the reference measurement.

Because of the conditions one has to deal with in practice, these sources of noise imply that it usually becomes necessary to use statistical methods for processing the measuring signals.

In order to illustrate the meaning of statistical processing herein, the following procedure is given as an example:

As a first step, the measuring signal is averaged for a number of time periods. Then 20 samples are taken in the measuring time interval ($T_1$ and $T_2$ in FIG. 4c). From among these samples, the five highest values and the five lowest are deleted from each group of 20 samples. The computer then calculates the arithmetic average value of the remaining 10 samples (of $E_1$ and $E_2$). Then $E = E_1 - E_2$ is calculated.

This sequence is repeated four times, so that four measuring values of E are produced. The highest and lowest values of E are deleted. The average arithmetic value of the two remaining values of E is then calculated.

Performance of a measurement in accordance with this procedure may last some minutes when ordinary laboratory equipment is being used. The required measuring time will be greatly reduced by means of special-built equipment and by applying a better procedure of averaging the numbers. In this respect, however, it should be noted that such measurements do allow a large consumption of time because the defects or phenomena that are to be monitored will not develop particularly rapid in the course of normal monitoring phases.

If excitation by a sinusoidal AC is used, the resulting measuring signal between two contact points will also become sinusoidal with an amplitude and phase that is dependent on the above mentioned conditions, i.e. the resistivity of the structural material, of skin effects and of induction in the measuring cables. Sinusoidal excitation current, however, requires other procedures for the signal treatment than that described above in connection with a rectangular shaped wave. For example, it is of essential importance to distinguish the signal components that are in phase with the excitation current and those being displaced 90° in relation to the same current.

The required comparison of deviations between the original signature and a measurement performed later can take place at different levels. At the lowermost level, individual measurements are compared with each other. In order to simplify the interpretation of the measured deviations, there may be a need for comparison in a more concentrated form. An essential point of the invention is that the total image of deviations between the signature and a later series of measurements, obtained by measurements on a relatively large number of contact points, be included in a manually or automatically performed consideration of the condition.

A possible graphical presentation form of measured results, i.e. deviations from the signature, is illustrated in FIGS. 5a-5d. The structural part to be monitored is presupposed therein to constitute a tube length, e.g. as shown in FIG. 2. FIGS. 5a-5d show the tube in an unfolded condition, and a network of squares with small circles in certain crossing points are drawn to mark contact points for measuring voltage drops. The figures in some of the squares represent measured deviations from the signature (in parts per thousand) on a tube with a diameter of 760 mm and with a wall thickness of approximately 25 mm. Blank squares mean that the measured deviation is equal to or less than ±3 parts per thousand, and an X indicates that measurements have not been performed to cover that position. Deviations which are less than 3 parts per thousand have not been reported in FIGS. 5a-5d because such small deviations may be due to uncertainties (noise) caused by the measuring arrangement.

Four situations have been represented: FIGS. 5a-5d corresponding to a lost cross sectional area of 2.5%; 5%, 10% and 15%, respectively. The investigated defect or crack appears from FIG. 5a where the crack has been indicated in the square showing a deviation of 7 parts per thousand. It appears from FIGS. 5a-5d that a development of a crack from 2.5% to 10 and 15% of the square sectional area results in a good indication in this representation so that it becomes possible to state in due time that an unfortunate development is going on. The proper location of the defect may as well be determined with a satisfactory certainty.

I claim:

1. A method of monitoring large metal structure in order to detect and localize defects which occur in the course of the lifetime of the structure, said method comprising the steps of: supplying an electric current to the structure or to a section thereof an initially measuring the voltage drops between a plurality of pairs of discrete contact points thereon when the structure is in an initial condition and free from any defects; subsequently making similar measurements of voltage drops when using the structure; comparing the subsequent measurements with the initial measurements; wherein the structure or a section thereof is equipped with a large number of fixed discrete contact points arranged in a pattern with a relatively uniform distribution over all of the structure or over all of the section which is to be monitored, and wherein each of the measurements are performed by supplying an electric current through at least two contact points on the structure or section thereof so as to measure the voltage drop between selected pairs of contact points from among an essential portion or all of said contact points, and wherein the total picture of deviations between initial measurements and subsequently performed measurements are used in the detection and localization of defects; wherein the supplied electric current is a pulse shaped DC current with such a low frequency that transients which occur as the current rises or falls, die before the current alternates again.

2. A method as claimed in claim 1, wherein the voltage drops are measured in time intervals such that transients which have occurred as the current rises or falls have substantially died so that an essentially stationary voltage drop is measured.

3. A method as claimed in claim 2, wherein an estimation of the actual value of the voltage drop between two points is produced by the statistical processing of many measurements on each of a number of measured voltage drops.

4. A method as claimed in claim 3, wherein the supplied electric current is a rectangular wave shaped AC with such a low frequency that transients which occur as the current rises or falls, die before the current alternates again.

5. A method as claimed in claim 1, wherein an estimation of the actual value of the voltage drop between two points is produced by the statistical processing of many measurements on each of a number of measured voltage drops.

6. A method for monitoring large metal structure in order to detect and localize defects which occur in the course of the lifetime of the structure, said method comprising the steps of: supplying an electric current to the structure or to a section thereof an initially measuring the voltage drops between a plurality of pairs of discrete contact points thereon when the structure is in an initial condition and free from any defects; subsequently making similar measurements of voltage drops when using the structure; comparing the subsequent measurements with the initial measurements; wherein the structure or a section thereof is equipped with a large number of fixed discrete contact points arranged in a pattern with a relatively uniform distribution over all of the structure or over all of the section which is to be monitored, and wherein each of the measurements are performed by supplying an electric current through at least two contact points on the structure or section thereof so as to measure the voltage drop between selected pairs of contact points from among an essential portion or all of said contact points, and wherein the total picture of deviations between initial measurements and subsequently performed measurements are used in the detection and localization of defects; wherein the supplied electric current is a rectangular wave shaped AC with such a low frequency that transients which occur as the current rises or falls, die before the current alternates again.

7. A method as claimed in claim 6, wherein the voltage drops are measured in time intervals such that transients which have occurred as the current rises or falls have substantially died so that an essentially stationary voltage drop is measured.

8. A method as claimed in claim 6, wherein an estimation of the actual value of the voltage drop between two points is produced by the statistical processing of many measurements on each of a number of measured voltage drops.

9. A method for monitoring large metal structure in order to detect and localize defects which occur in the course of the lifetime of the structure, said method comprising the steps of: supplying an electric current to the structure or to a section thereof an initially measuring the voltage drops between a plurality of pairs of discrete contact points thereon when the structure is in an initial condition and free from any defects; subsequently making similar measurements of voltage drops when using the structure; comparing the subsequent measurements with the initial measurements; wherein the structure or a section thereof is equipped with a large number of fixed discrete contact points arranged in a pattern with a relatively uniform distribution over all of the structure or over all of the section which is to be monitored, and wherein each of the measurements are performed by supplying an electric current through at least two contact points on the structure or section thereof so as to measure the voltage drop between selected pairs of contact points from among an essential portion or all of said contact points, and wherein the total picture of deviations between initial measurements and subsequently performed measurements are used in the detection and localization of defects; wherein the voltage drops are measured in time intervals such that transients which have occurred as the current rises or falls have substantially died so that an essentially stationary voltage drop is measured.

10. A method as claimed in claim 9, wherein an estimation of the actual value of the voltage drop between two points is produced by the statistical processing of many measurements on each of a number of measured voltage drops.

11. A method for monitoring large metal structure in order to detect and localize defects which occur in the course of the lifetime of the structure, said method comprising the steps of: supplying an electric current to the structure or to a section thereof an initially measuring the voltage drops between a plurality of pairs of discrete contact points thereon when the structure is in an initial condition and free from any defects; subsequently making similar measurements of voltage drops when using the structure; comparing the subsequent measurements with the initial measurements; wherein the structure or a section thereof is equipped with a large number of fixed discrete contact points arranged in a pattern with a relatively uniform distribution over all of the structure or over all of the section which is to be monitored, and wherein each of the measurements are performed by supplying an electric current through at least two contact points on the structure or section thereof so as to measure the voltage drop between selected pairs of contact points from among an essential portion or all of said contact points, and wherein the total picture of deviations between initial measurements and subsequently performed measurements are used in the detection and localization of defects; wherein an estimation of the actual value of the voltage drop between two points is produced by the statistical processing of many measurements on each of a number of measured voltage drops.

12. A method as claimed in claim 11, wherein the voltage drops are measured in time intervals such that transients which have occurred as the current rises or falls have substantially died so that an essentially stationary voltage drop is measured.

13. A method for monitoring large metal structure in order to detect and localize defects which occur in the course of the lifetime of the structure, said method comprising the steps of: supplying an electric current to the structure or to a section thereof an initially measuring the voltage drops between a plurality of pairs of discrete contact points thereon when the structure is in an initial condition and free from any defects; subsequently making similar measurements of voltage drops when using the structure; comparing the subsequent measurements with the initial measurements; wherein the structure or a section thereof is equipped with a large number of fixed discrete contact points arranged in a pattern with a relatively uniform distribution over all of the structure or over all of the section which is to be monitored, and wherein each of the measurements are performed by supplying an electric current through at least two contact points on the structure or section thereof so as to measure the voltage drop between selected pairs of contact points from among an essential portion or all of said contact points, and wherein the total picture of deviations between initial measurements and subsequently performed measurements are used in the detection and localization of defects; wherein the electric current is supplied in sequence through two and two mutually far spaced contact points selected among from a selected portion of fixed contact points.

14. A method as claimed in claim 13, wherein the voltage drops are measured in time intervals such that transients which have occurred as the current rises or falls have substantially died so that an essentially stationary voltage drop is measured.

15. A method as claimed in claim 13, wherein an estimation of the actual value of the voltage drop between two points is produced by the statistical processing of many measurements on each of a number of measured voltage drops.

16. A device for detected and localizing defects in large metal structures comprising an electric excitation circuit for supplying an electric current to the metal structure or a section thereof and a measuring circuit for measuring corresponding voltage drops between contact points which are located on the structure, wherein a large number of fixed discrete contact points are arranged in a pattern with a relatively uniform distribution over the area to be monitored, and wherein the measuring circuit comprises a multiplexer arranged to perform change-overs for measuring voltage drops between selected pairs of contact points which are selected from among an essential portion or all of said contact points, and wherein a control unit is arranged to control the supplying of the electric current from the electric excitation circuit and to control change-overs of the multiplexer and the presentation of the measured results; wherein at least a considerable portion of the contact points are arranged so that they can both serve to measure voltage drops and to supply the electric current from the excitation circuit.

17. A device for detecting and localizing defects in large metal structures comprising an electric excitation circuit for supplying an electric current to the metal structure or a section thereof and a measuring circuit for measuring corresponding voltage drops between contact points which are located on the structure, wherein a large number of fixed discrete contact points are arranged in a pattern with a relatively uniform distribution over the area to be monitored, and wherein the measuring circuit comprises a multiplexer arranged to perform change-overs for measuring voltage drops between selected pairs of contact points which are selected from among an essential portion or all of said contact points, and wherein a control unit is arranged to control the supplying of the electric current from the electric excitation circuit and to control change-overs of the multiplexer and the presentation of the measured results; wherein the control unit comprises a computer arranged to produce an estimation of the actual value of the voltage drop between two points by the statistical processing of many measurements on each of a number of measured voltage drops.

18. A device as claimed in claim 17, wherein at least a considerable portion of the contact points are arranged so that they can serve both to measure voltage drops and to supply the electric current from the excitation circuit.

* * * * *